(12) United States Patent
Pimenta

(10) Patent No.: US 7,887,595 B1
(45) Date of Patent: Feb. 15, 2011

(54) METHODS AND APPARATUS FOR SPINAL FUSION

(75) Inventor: Luiz Pimenta, Sao Paulo (BR)

(73) Assignee: NuVasive, Inc., San Diego, CA (US)

( * ) Notice: Subject to any disclaimer, the term of this patent is extended or adjusted under 35 U.S.C. 154(b) by 106 days.

(21) Appl. No.: 11/634,440

(22) Filed: Dec. 5, 2006

Related U.S. Application Data

(60) Provisional application No. 60/742,865, filed on Dec. 5, 2005.

(51) Int. Cl.
*A61F 2/44* (2006.01)
(52) U.S. Cl. .................. 623/17.16; 623/17.11; 606/249
(58) Field of Classification Search ................. 606/60, 606/61, 246–249, 279, 280–299; 623/17.11–17.16
See application file for complete search history.

(56) References Cited

U.S. PATENT DOCUMENTS

| | | | |
|---|---|---|---|
| 4,493,317 A | 1/1985 | Klaue | |
| 4,599,999 A | 7/1986 | Klaue | |
| 4,743,256 A | 5/1988 | Brantigan | |
| 4,904,261 A | 2/1990 | Dove et al. | |
| 4,955,908 A | 9/1990 | Frey et al. | |
| 5,364,399 A | 11/1994 | Lowery et al. | |
| 5,397,364 A | 3/1995 | Kozak et al. | |
| 5,405,391 A | 4/1995 | Hednerson et al. | |
| 5,423,826 A | 6/1995 | Coates et al. | |
| 5,507,801 A | 4/1996 | Gisin et al. | |
| 5,578,034 A | 11/1996 | Estes | |
| 5,601,553 A | 2/1997 | Trebing et al. | |
| 5,616,144 A | 4/1997 | Yapp et al. | |
| 5,713,899 A | 2/1998 | Marnay et al. | |
| 5,755,721 A | 5/1998 | Hearn | |
| 5,772,661 A | 6/1998 | Michelson | |
| 5,851,207 A | 12/1998 | Cesarone | |
| 5,876,402 A | 3/1999 | Errico et al. | |
| 5,888,223 A | 3/1999 | Bray | |
| 5,916,267 A | 6/1999 | Tienboon | |
| 5,931,838 A | 8/1999 | Vito | |
| 5,951,558 A | 9/1999 | Fiz | |
| 5,954,722 A | 9/1999 | Bono | |
| 6,066,175 A | 5/2000 | Henderson et al. | |
| 6,080,193 A | 6/2000 | Hochshuler et al. | |
| 6,093,205 A | 7/2000 | McLeod et al. | |
| 6,120,503 A | 9/2000 | Michelson | |
| 6,136,001 A | 10/2000 | Michelson | |
| 6,139,550 A | 10/2000 | Michelson | |
| 6,152,927 A | 11/2000 | Farris et al. | |
| 6,156,037 A | 12/2000 | LeHuec et al. | |
| 6,159,214 A * | 12/2000 | Michelson ................... | 606/80 |
| 6,193,721 B1 | 2/2001 | Michelson | |
| 6,210,415 B1 | 4/2001 | Bester | |
| 6,228,118 B1 | 5/2001 | Gordon | |

(Continued)

FOREIGN PATENT DOCUMENTS

EP        0179695 B1      3/1989

(Continued)

*Primary Examiner*—Eduardo C Robert
*Assistant Examiner*—Christina Negrelli
(74) *Attorney, Agent, or Firm*—Jonathan Spangler

(57) ABSTRACT

A spinal fusion implant of non-bone construction to be introduced into an intervertebral disc space for the promotion of spinal fusion.

25 Claims, 3 Drawing Sheets

U.S. PATENT DOCUMENTS

| | | | |
|---|---|---|---|
| 6,235,034 B1 | 5/2001 | Bray | |
| 6,235,059 B1 | 5/2001 | Benezech et al. | |
| 6,261,291 B1 | 7/2001 | Talaber et al. | |
| 6,306,139 B1 | 10/2001 | Fuentes | |
| 6,306,170 B2 | 11/2001 | Ray | |
| 6,331,179 B1 | 12/2001 | Freid et al. | |
| 6,342,055 B1 | 1/2002 | Eisermann et al. | |
| 6,342,057 B1 | 1/2002 | Brace et al. | |
| 6,364,880 B1 | 4/2002 | Michelson | |
| 6,379,364 B1 | 4/2002 | Brace et al. | |
| 6,398,783 B1 | 6/2002 | Michelson | |
| 6,413,259 B1 | 7/2002 | Lyons et al. | |
| 6,432,106 B1 | 8/2002 | Fraser | |
| 6,454,771 B1 | 9/2002 | Michelson | |
| 6,461,359 B1 | 10/2002 | Tribus et al. | |
| 6,471,724 B2 | 10/2002 | Zdeblick et al. | |
| 6,485,517 B1 | 11/2002 | Michelson | |
| 6,527,776 B1 | 3/2003 | Michelson | |
| 6,540,785 B1 * | 4/2003 | Gill et al. | 623/17.14 |
| 6,558,423 B1 | 5/2003 | Michelson | |
| 6,562,073 B2 | 5/2003 | Foley | |
| 6,572,619 B2 | 6/2003 | Santilli | |
| 6,576,017 B2 | 6/2003 | Foley et al. | |
| 6,579,290 B1 | 6/2003 | Hardcastle et al. | |
| 6,582,468 B1 | 6/2003 | Gauchet | |
| 6,602,255 B1 | 8/2003 | Campbell et al. | |
| 6,629,998 B1 | 10/2003 | Lin | |
| 6,669,700 B1 | 12/2003 | Farris et al. | |
| 6,682,563 B2 | 1/2004 | Scharf | |
| 6,692,503 B2 | 2/2004 | Foley et al. | |
| 6,695,846 B2 | 2/2004 | Richelsoph et al. | |
| 6,712,818 B1 | 3/2004 | Michelson | |
| 6,730,127 B2 * | 5/2004 | Michelson | 623/17.16 |
| 6,773,460 B2 | 8/2004 | Jackson | |
| 6,837,905 B1 | 1/2005 | Lieberman | |
| 6,896,676 B2 | 5/2005 | Zubok et al. | |
| 6,916,320 B2 | 7/2005 | Michelson | |
| 6,936,050 B2 | 8/2005 | Michelson | |
| 6,936,051 B2 | 8/2005 | Michelson | |
| 6,972,019 B2 | 12/2005 | Michelson | |
| 7,001,387 B2 | 2/2006 | Farris et al. | |
| 7,001,389 B1 | 2/2006 | Navarro et al. | |
| 7,004,944 B2 | 2/2006 | Gause | |
| 7,033,394 B2 | 4/2006 | Michelson | |
| 7,041,135 B2 | 5/2006 | Michelson | |
| 7,048,739 B2 | 5/2006 | Konieczynski et al. | |
| 7,060,067 B2 | 6/2006 | Needham et al. | |
| 7,112,222 B2 | 9/2006 | Fraser et al. | |
| 7,137,984 B2 | 11/2006 | Michelson | |
| 7,163,561 B2 | 1/2007 | Michelson | |
| 7,172,627 B2 | 2/2007 | Fiere et al. | |
| 7,182,782 B2 | 2/2007 | Kirschman | |
| 7,204,837 B2 | 4/2007 | Paul | |
| 7,232,464 B2 | 6/2007 | Mathieu et al. | |
| 7,238,203 B2 | 7/2007 | Bagga et al. | |
| 7,255,698 B2 | 8/2007 | Michelson | |
| 7,320,708 B1 | 1/2008 | Bernstein | |
| 7,331,994 B2 | 2/2008 | Gordon | |
| 7,354,452 B2 | 4/2008 | Foley | |
| 7,452,370 B2 | 11/2008 | Anderson | |
| 7,618,456 B2 | 11/2009 | Mathieu et al. | |
| 7,662,174 B2 | 2/2010 | Doubler et al. | |
| 2002/0004683 A1 * | 1/2002 | Michelson | 623/17.16 |
| 2002/0045945 A1 * | 4/2002 | Liu et al. | 623/17.16 |
| 2002/0058944 A1 * | 5/2002 | Michelson | 606/79 |
| 2002/0107571 A1 * | 8/2002 | Foley | 623/17.11 |
| 2003/0083667 A1 | 5/2003 | Ralph | |
| 2003/0187440 A1 | 10/2003 | Richelsoph | |
| 2003/0208274 A1 * | 11/2003 | Davis | 623/17.16 |
| 2003/0225409 A1 | 12/2003 | Freid | |
| 2004/0039387 A1 | 2/2004 | Gause | |
| 2004/0039448 A1 * | 2/2004 | Pisharodi | 623/17.15 |
| 2004/0068318 A1 * | 4/2004 | Coates et al. | 623/17.11 |
| 2004/0176776 A1 * | 9/2004 | Zubok et al. | 606/96 |
| 2004/0186482 A1 | 9/2004 | Kolb | |
| 2004/0193272 A1 | 9/2004 | Zubok | |
| 2004/0210232 A1 | 10/2004 | Patel | |
| 2004/0210314 A1 * | 10/2004 | Michelson | 623/17.16 |
| 2004/0215195 A1 | 10/2004 | Shipp | |
| 2004/0267274 A1 | 12/2004 | Patel | |
| 2005/0015092 A1 | 1/2005 | Rathbun | |
| 2005/0015093 A1 | 1/2005 | Suh | |
| 2005/0027301 A1 | 2/2005 | Stihl | |
| 2005/0033294 A1 | 2/2005 | Garden | |
| 2005/0038444 A1 | 2/2005 | Binder | |
| 2005/0043738 A1 | 2/2005 | Ryan | |
| 2005/0049593 A1 | 3/2005 | Duong | |
| 2005/0085913 A1 * | 4/2005 | Fraser et al. | 623/17.11 |
| 2005/0137606 A1 | 6/2005 | Binder | |
| 2005/0143824 A1 | 6/2005 | Richelsoph | |
| 2005/0234455 A1 | 10/2005 | Binder et al. | |
| 2005/0261690 A1 | 11/2005 | Binder et al. | |
| 2006/0030851 A1 | 2/2006 | Bray | |
| 2006/0079961 A1 | 4/2006 | Michelson | |
| 2006/0100637 A1 | 5/2006 | Rathbun | |
| 2006/0129244 A1 | 6/2006 | Salt | |
| 2006/0206208 A1 | 9/2006 | Michelson | |
| 2006/0224241 A1 | 10/2006 | Butler | |
| 2006/0235403 A1 | 10/2006 | Blain | |
| 2006/0235409 A1 | 10/2006 | Blain | |
| 2007/0055252 A1 | 3/2007 | Blain | |
| 2007/0233120 A1 | 10/2007 | Thramann | |
| 2008/0097433 A1 | 4/2008 | Molz | |
| 2008/0119933 A1 | 5/2008 | Aebi et al. | |
| 2008/0161925 A1 | 7/2008 | Brittan | |
| 2008/0177307 A1 | 7/2008 | Moskowitz | |
| 2008/0249569 A1 | 10/2008 | Waugh et al. | |
| 2008/0249575 A1 | 10/2008 | Waugh et al. | |
| 2008/0249625 A1 | 10/2008 | Waugh et al. | |
| 2008/0287999 A1 | 11/2008 | Markworth | |
| 2008/0306596 A1 | 12/2008 | Jones | |
| 2009/0088849 A1 | 4/2009 | Armstrong et al. | |
| 2009/0210064 A1 | 8/2009 | Lechmann et al. | |
| 2009/0264934 A1 | 10/2009 | Youssef et al. | |
| 2010/0042159 A1 | 2/2010 | Butler | |
| 2010/0057206 A1 | 3/2010 | Duffield et al. | |
| 2010/0087925 A1 | 4/2010 | Kostuik et al. | |
| 2010/0094421 A1 | 4/2010 | Mathieu et al. | |
| 2010/0121383 A1 | 5/2010 | Midland | |

FOREIGN PATENT DOCUMENTS

| | | |
|---|---|---|
| WO | 2007098288 A2 | 8/2007 |
| WO | 2008065450 | 6/2008 |
| WO | 2009064644 A1 | 5/2009 |
| WO | 2009148421 A1 | 12/2009 |
| WO | 2010028095 A1 | 3/2010 |
| WO | 2010054181 A1 | 5/2010 |
| WO | 2010054208 A1 | 5/2010 |

* cited by examiner

METHODS AND APPARATUS FOR SPINAL FUSION

CROSS REFERENCES TO RELATED APPLICATIONS

The present application is a nonprovisional patent application claiming benefit under 35 U.S.C. §119(e) from U.S. Provisional Application Ser. No. 60/742,865, filed on Dec. 5, 2005, the entire contents of which are hereby expressly incorporated by reference into this disclosure as if set forth fully herein.

BACKGROUND OF THE INVENTION

I. Field of the Invention

The present invention relates generally to spinal surgery and, more particularly, to a device for spinal fusion comprising a spinal fusion implant of non-bone construction to be introduced into an intervertebral disc space.

II. Discussion of the Prior Art

Currently there are nearly 500,000 spine lumbar and cervical fusion procedures performed each year in the United States. One of the causes of back pain and disability results from the rupture or degeneration of one or more intervertebral discs in the spine. Surgical procedures are commonly performed to correct problems with displaced, damaged, or degenerated intervertebral discs due to trauma, disease, or aging. Generally, spinal fusion procedures involve removing some or the all of the diseased or damaged disc, and inserting one or more intervertebral implants into the resulting disc space.

Minimally invasive methods of performing spinal fusion have gained popularity in recent years due to the many benefits of the procedure which include diminished dissection of body tissue and lower blood loss during surgery resulting in reduced surgery time, lower post-operative pain and a quicker recovery for patients. Anterior lumbar interbody fusion (ALIF) procedures provide access to a desired target site without harming back muscles and nerves. The ALIF technique involves approaching the spine through the abdomen and exposing the front of the spine, as opposed to the side or the back. Approaching the spine this way generally allows for greater exposure and a more complete excision of the damaged disc. Introducing the intervertebral implant serves to restore the height between adjacent vertebrae ("disc height"), which reduces if not eliminates neural impingement commonly associated with a damaged or diseased disc. Distraction of the disc space with subsequent decompression of nerve roots can be accomplished by rotating a device between the adjacent vertebrae.

Current spinal fusion implants utilize grafts of either bone or artificial implants to fill the intervertebral disc space. Spinal fusion implants or grafts may be made of metal, plastic composites, ceramics, or bone. Natural bone grafts have also been developed including autologous and allograft bone grafts. Other bone grafts may include certain man-made substances including binder joining bone chips and composite bone structures.

While generally effective, the use of bone grafts presents several disadvantages. Autologous bone grafts are obtained from bone material surgically removed from the iliac crest of a patient. This method can be detrimental because it may not yield a sufficient quantity of graft material, requires additional surgery, and increases the risk of infection and blood loss. Moreover, the structural integrity at the donor site can be reduced and significant morbidity associated with harvesting the autologous bone graft may occur.

Allograft bone grafts are obtained from cadaveric specimens, machined, and sterilized for implantation. However, allografts can be disadvantageous because of the risk of disease transmission and immune reactions. Further, production of allograft bone implants may be difficult because of the inherent challenges in forecasting the receipt of cadavers and allograft may only provide temporary support as it is difficult to manufacture the allograft with consistent shape and strength given the differing characteristics of cadavers. Graft material usually has a smooth surface which does not provide a good friction fit between the adjacent vertebrae and slippage of the graft may occur which can cause neural and vascular injury as well as collapse of the disc space.

A need remains for fusion implants that preserve the intradiscal space and support the vertebral column until the adjacent vertebrae are fused and still encourage bone ingrowth to achieve a solid fusion. A need also remains for implants which maximize surface contact with outer portions of vertebral anatomy while providing maximum area for fusion.

The present invention is directed at overcoming, or at least improving upon, the disadvantages of the prior art.

SUMMARY OF THE INVENTION

The present invention overcomes the drawbacks of the prior art by providing a spinal fusion implant for placement between adjacent vertebral bodies. The present invention facilitates enhanced ring contact and fit between anterior ring portions of vertebral endplates. The spinal fusion implant of the present invention may comprise of any suitable non-bone composition, including but not limited to polymer compositions (e.g. poly-ether-ether-ketone (PEEK) and/or poly-ether-ketone-ketone (PEKK)), ceramic, metal, or any combination of these materials. The spinal fusion implant of the present invention may be provided in any number of suitable shapes and sizes depending upon the particular surgical procedure or need. The spinal fusion implant may be dimensioned for use in the spine without departing from the scope of the present invention.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein.

DESCRIPTION OF THE PREFERRED EMBODIMENT

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The spinal fusion implant disclosed herein boasts a variety of inventive features and components that warrant patent protection, both individually and in combination.

Figure 1:
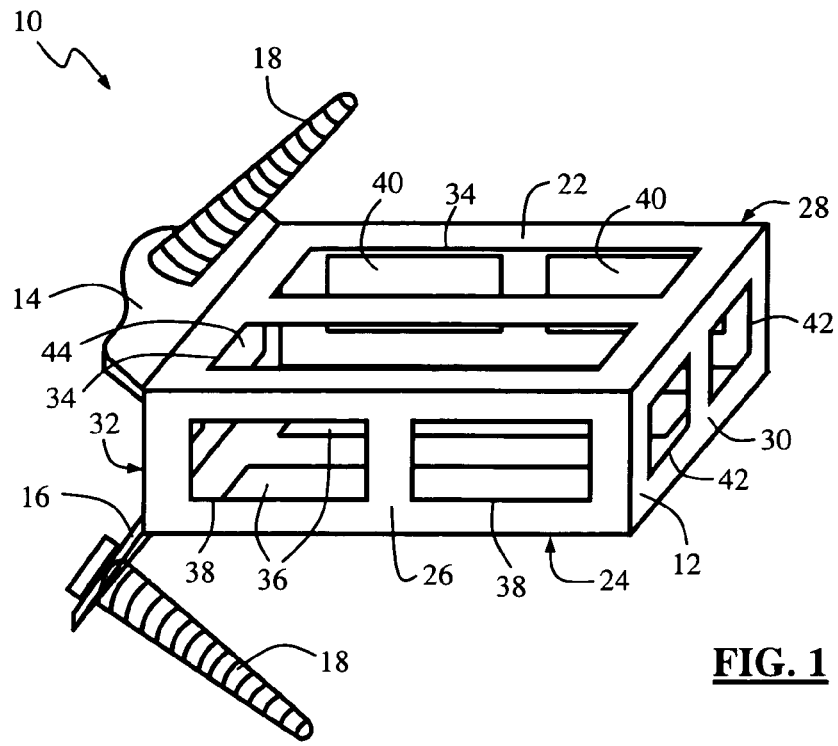
FIG. 1 is a perspective view of an example of a spinal fusion implant according to one embodiment of present invention.
Figure 2:
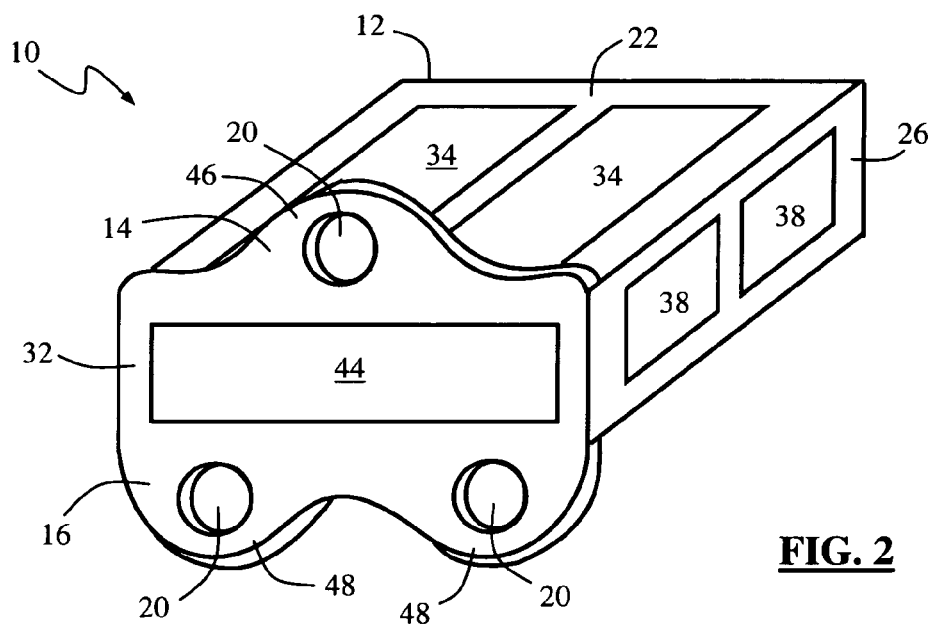
FIG. 2 is another perspective view of the spinal fusion implant of FIG. 1.
Figure 3:
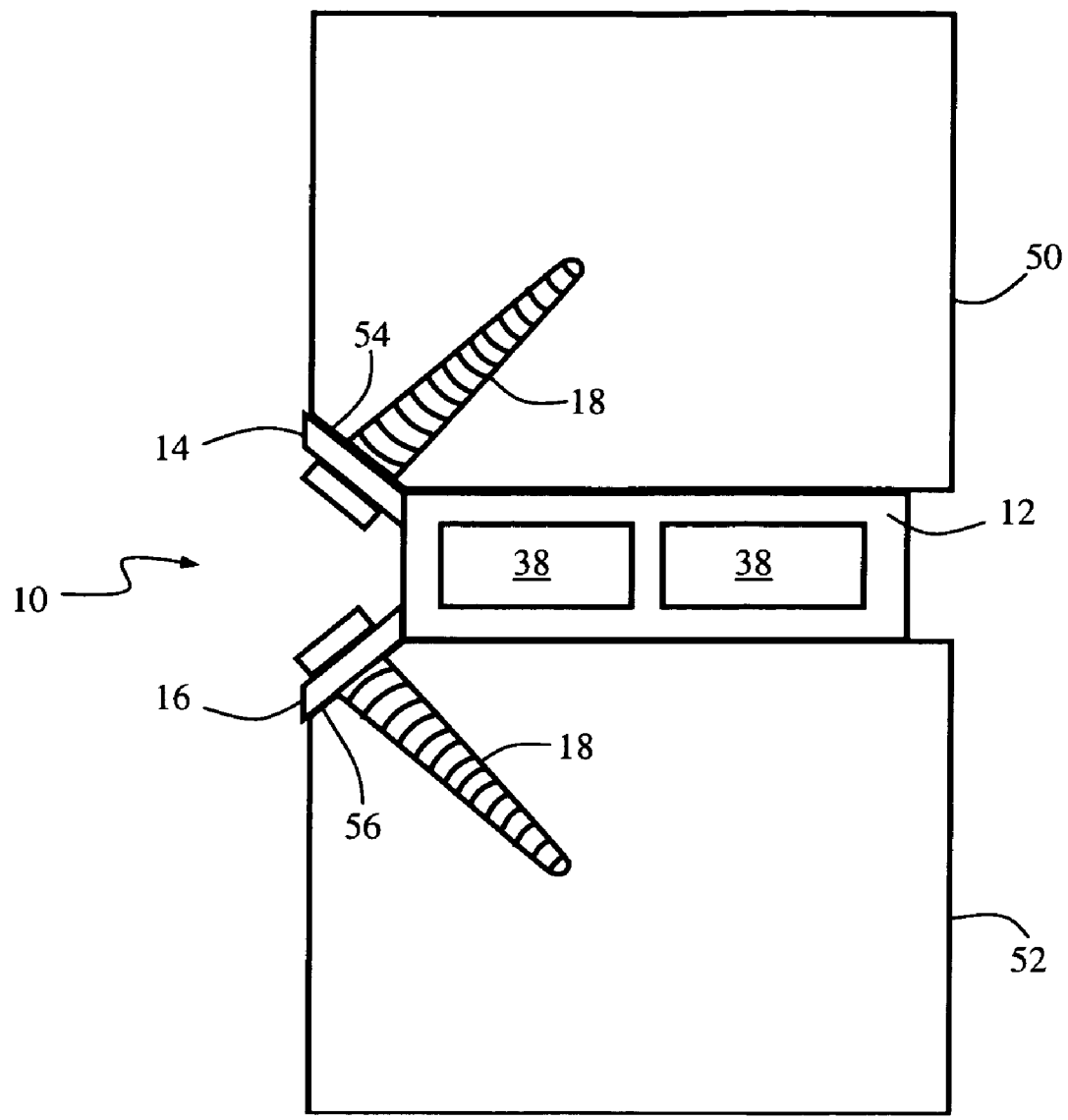
FIG. 3 is a side view of the spinal fusion implant of FIG. 1 inserted into an intervertebral space according to one embodiment of the present invention.

FIGS. 1-2 illustrate a spinal fusion implant 10 according to a first broad aspect of the present invention. The spinal fusion implant 10 of the present invention includes a body 12, a first flange 14, a second flange 16, and a plurality of bone anchor elements 18. According to one embodiment described herein by way of example only, the spinal fusion implant 10 may be provided with varying length and width dimensions depending upon the size of the targeted disc space of a patient. The spinal fusion implant 10 may be constructed of any suitable non-bone composition having suitable radiolucent characteristics, including but not limited to polymer compositions (e.g. poly-ether-ether-ketone (PEEK) and/or poly-ether-ketone-ketone (PEKK)) or any combination of PEEK and PEKK, plastics, and/or ceramics. As shown in FIG. 3, the spinal fusion implant 10 of the present invention is dimensioned to be received within an intervertebral space defined by adjacent first and second vertebral bodies 50, 52.

As illustrated by way of example in FIGS. 1-2, the body 12 may have a generally rectangular shape including first and second contact surfaces 22, 24, first and second lateral sides 26, 28, a leading end 30 and a trailing end 32. Each of the first and second contact surfaces 22, 24 may include at least one aperture 34, 36, respectively, described in further detail below. Each of the first and second lateral sides may include at least one aperture 38, 40, respectively, described in further detail below. The leading and trailing ends 30, 32 may include at least one aperture 42, 44, respectively, described in further detail below. The body 12 of the present invention may be provided in any number of suitable shapes and sizes depending upon the needs of a particular patient. By way of example only, the body 12 may be shaped with rounded edges and curved sides to conform to the natural curvature of the vertebral endplates and/or intervertebral space.

As will be appreciated by one skilled in the art, the apertures 34, 36, 38, 40, 42 and 44 may be provided in any of a variety of suitable geometric shapes in addition to the rectangular shape shown, including but not limited to oblong, triangular, circular, polygonal and/or any combination thereof. It should be noted that one or more apertures 34, 36, 38, 40, 42 and 44 may be included on each of first and second contact surfaces 22, 24, first and second lateral sides 26, 28 and leading and trailing ends 30, 32, respectively. In the example depicted in FIGS. 1-2, the first contact surface 22 includes two apertures 34, the second contact surface 24 includes two apertures 36, the first lateral side 26 includes two apertures 38, the second lateral side 28 includes two apertures 40, the leading end 30 includes two apertures 42 and the trailing end 34 includes one aperture 44. It should be appreciated that the apertures 34, 36, 38, 40, 42 and 44 included on the body 12 in each respective location (i.e. first and second contact surfaces 22, 24, first and second lateral sides 26, 28 and leading and trailing ends 30, 32) may be provided in any desirable number and combination. The apertures 34, 36, 38, 40, 42 and 44 are an additional feature for promoting fusion between the first and second vertebral bodies by allowing a boney bridge to form through the spinal fusion implant 10. Apertures 34, 36, 38, 40, 42 and 44 also allow a surgeon to better visualize and/or assess the degree of fusion when conducting radiographic assessment (e.g. x-ray, fluoroscopy, etc. . . . ).

The first flange 14 includes at least one lip 46 having at least one anchor aperture 20 dimensioned to receive a bone anchor element 18 for securing the spinal fusion implant 10 to the first vertebral body 50. By way of example only, the first flange 14 is configured to contact a portion of the anterior aspect of the first vertebral body. According to one embodiment of the present invention, a portion of the anterior aspect of the first vertebral body 50 may be removed to create a first generally angled engagement surface 54 (FIG. 3) to improve the degree of contact between the first flange 14 and the first vertebral body 50. Preferably, the first generally angled engagement surface 54 is formed at an angle between 15 and 75 degrees, inclusive, measured relative to the vertebral endplate. As such, the first flange 14 extends from the body 12 at an angle complementary to that of the first generally angled engagement surface 54 (e.g. between 15 and 75 degrees, inclusive). Optionally, the first flange 14 may be angularly adjustable to accommodate any specific angle at which the first generally angled engagement surface 54 is formed.

The first flange 14 may be provided in any manner of sizes and widths to provide optimal contact between the flange 14 and the first vertebral body 50. For example, the lip 46 may be sized so as to contact any portion of the width and/or height of the first vertebral body 50. The example of the spinal fusion implant 10 illustrated in FIGS. 1-4 depict a first flange 14 having a lip 46 dimensioned to contact approximately one-half of the width of the first vertebral body 50. However, other configurations in which the lip 46 is dimensioned to contact more or less than one-half of the width of the first vertebral body 50 are possible. For example, the first flange 14 may be provided with more than one lip 46. The first flange 14 and/or the lip 46 may be provided in any number of suitable shapes to provide optimal contact between the flange 14 and the vertebral body 50, including but not limited to (and by way of example only) semi-circular, rectangular, and/or any other full or partial geometric shape. Also, the first flange 14 and/or lip 46 may be provided with rounded corners such as to eliminate any sharp edges or surfaces in order to protect from damaging any adjacent human tissue. It is also contemplated that first flange 14 may be pre-attached, molded to and/or otherwise integrated as a single piece with the body 12. Additionally, while the lip 46 is shown and described herein by example as having a single anchor aperture 20, it is contemplated that the lip 46 may have any number of anchor apertures 20 to accommodate optional insertion of additional bone anchor elements 18.

The second flange 16 includes at least one lip 48 having at least one anchor aperture 20 dimensioned to receive a bone anchor element 18 for securing the spinal fusion implant 10 to a second vertebral body 52. The second flange 16 is configured to contact a portion of the anterior aspect of the second vertebral body 52. According to one embodiment of the present invention, a portion of the second vertebral body may be removed to create a second generally angled engagement surface 56 (FIG. 3) to improve the degree of contact between the second flange 16 and the second vertebral body 52. Preferably, the second generally angled engagement surface 56 is formed at an angle between 15 and 75 degrees, inclusive, measured relative to the vertebral endplate. As such, the second flange 16 extends from the body 12 at an angle complementary to that of the second generally angled engagement surface 56 (e.g. between 15 and 75 degrees, inclusive). Optionally, the second flange 16 may be angularly adjustable to accommodate any specific angle at which the first generally angled engagement surface 56 is formed.

The second flange 16 may be provided in any manner of sizes and widths to provide optimal contact between the flange 16 and the vertebral body 52. For example, the lip 48 may be sized so as to contact substantially the whole of the second vertebral body 52. The example of the spinal fusion implant 10 illustrated in FIGS. 1-4 depict a second flange 16 having a pair of lips 48, each having a single anchor aperture 20, and configured in total to contact substantially the entire width of the second vertebral body 52. However, other configurations in which the lip(s) 48 are dimensioned to contact less than substantially the entire width of the second vertebral body 52 are possible. For example, the second flange 16 may be provided with only one lip 48 or more than two lips 48. The second flange 16 and/or the lip(s) 48 may be provided in any number of suitable shapes to provide optimal contact between the flange 16 and the vertebral body 52, including but not limited to (and by way of example only) semi-circular, rectangular, and/or any other full or partial geometric shape. Also, the second flange 16 and/or lip(s) 48 may be provided with rounded corners such as to eliminate any sharp edges or surfaces in order to protect from damaging any adjacent human tissue. It is also contemplated that second flange 16 may be pre-attached, molded to and/or otherwise integrated as a single piece with the body 12. Additionally, while each lip 48 is shown and described herein by example as having a single anchor aperture 20, it is contemplated that the lip(s) 48 may have any number of anchor apertures 20 to accommodate optional insertion of additional bone anchor elements 18.

Each anchor aperture 20 on the first and second flanges 14, 16 is dimensioned to receive a bone anchor element 18. While the shape of each anchor aperture 20 is illustrated herein as being circular, it should be noted that other shapes are possible, such as elongated holes or any other suitably shaped apertures that perform a similar function. The anchor aperture 20 may also be set at an angle so as to allow the bone anchor element 18 to achieve the best possible purchase into the first and second vertebral bodies 50, 52. The bone anchor element 18 according to one embodiment of the present invention may be either a fixed angle bone screw or a variable angle bone screw. Fixed angle bone screws and variable angle bone screws are generally known in the art and will not be further explained herein. Alternatively, the bone anchor elements 18 may include pins, nails, tacks, hooks and the like.

Although not shown, it will be appreciated as being within the scope of the present invention to provide the implant 10 with any number of anti-backout mechanisms to prevent the bone anchor elements 18 from backing out of the first and second vertebral bodies 50, 52 over time. By way of example only, this may be accomplished by equipping each flange 14, 16 with a cover or lip or feature to prevent the head of the bone anchor element 18 from translating proximally after implantation into a vertebral body, such as a set screw placed within the anchor aperture 20 to cover the head of bone anchor element 18 and/or a rotating cover element that can be manipulated at least partially over the head of the bone anchor element 18 after the bone anchor element 18 has been implanted.

Figure 4:
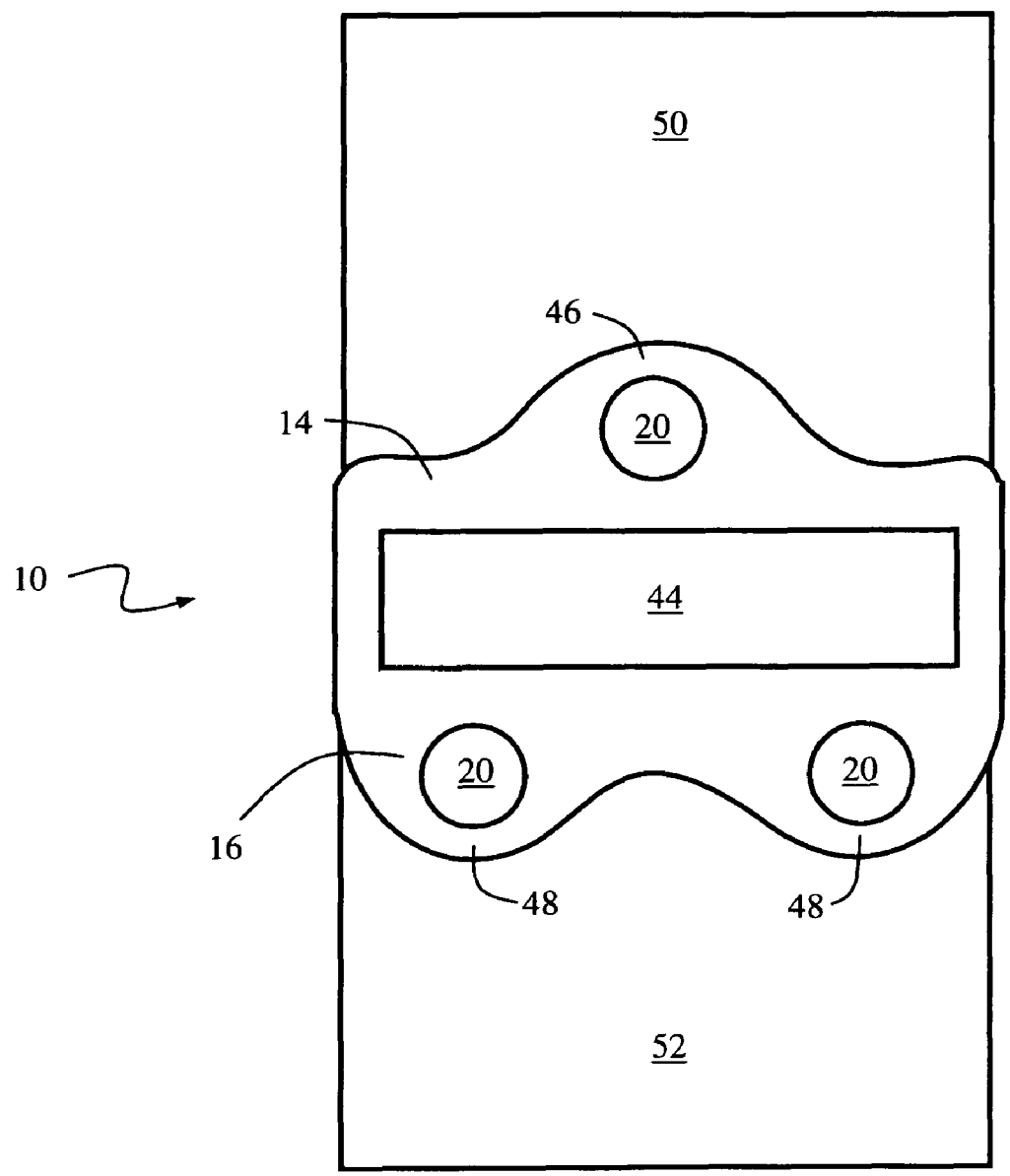
FIG. 4 is a front view of the spinal fusion implant of FIG. 1 inserted into an intervertebral space according to one embodiment of the present invention.

FIGS. 3-4 illustrate a side and front view, respectively, of a spinal fusion implant 10 of the present invention in use between two vertebral bodies 50, 52. As illustrated in FIGS. 3-4, the spinal fusion implant 10 of the present invention may be used to provide temporary or permanent fixation along an orthopedic target site. To do so, the spinal fusion implant 10 may be introduced into a disc space while locked to a surgical insertion instrument and thereafter employed in the proper orientation and released. The exemplary spinal fusion implant 10 having been deposited in the disc space, effects spinal fusion over time as the natural healing process integrates and binds the implant.

According to a broad aspect of the present invention, the spinal fusion implant 10 may be introduced into a spinal target site through use of any of a variety of suitable surgical instruments having the capability to engage the spinal implant. A clinician may utilize the implant 10 in a minimally invasive spinal fusion procedure. After creation of a working channel to the target disc space, the disc space is prepared for receiving the spinal fusion implant 10 by removing any portions of the intervertebral disc that may be present. At this point it may be desirable to prepare portions of the anterior aspects of the first and second vertebrae 50, 52 adjoining the target disc space. This preparation may include the removal of selected portions (e.g. from an endplate to an anterior surface) from the first and second vertebral bodies 50, 52 so as to create first and second generally angled engagement surfaces 54, 56. Preferably, the angled portions are formed substantially within cortical bone portions of the vertebral bodies 50, 52. Thus, the present invention facilitates enhanced ring contact and fit between anterior portions of vertebral endplates. This in turn enables the bone anchor elements 18 to achieve superior purchase within the vertebral bodies 50, 52. A single spinal fusion device 10 is then placed into the intervertebral disc space. Additional materials and tools may be included in the procedure before, during, or after the insertion of the implant 10 to aid in introducing the implant into a targeted spinal site.

Once the spinal fusion implant 10 has been introduced into the disc space, the first and second flanges 14, 16, will be positioned to contact the first and second vertebral bodies 50, 52 along the first and second generally angled engagement surfaces 54, 56 due to the removal of angled portions from the vertebral bodies. These angled cuts on the vertebral bodies enable greater purchase of the bone anchor elements 18 within the vertebral bodies and thus allow for a more effective fusion of the vertebral bodies 50, 52.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the invention is to cover all modifications, equivalents, and alternatives falling within the spirit and scope of the invention as defined herein.

What is claimed is:

1. A spinal fusion implant dimensioned to occupy an intervertebral space between a first vertebral body and a second vertebral body, comprising:
   a body portion having first and second contact surfaces, first and second lateral sides, a leading end and a trailing end;
   a first flange comprising a lip extending from said body at an interface between said first contact surface and said trailing end, said lip being generally centered between said first and second lateral sides and extending laterally to points short of said first and second sides; and
   a second flange comprising a pair of lips extending from said body at an interface between said second contact surface and said trailing end, said first lip of the pair extending laterally from said first lateral surface to a point short of the center of said trailing end and said second lip of the pair extending generally laterally from said second lateral side to a point short of center of said trailing end such that said first and second lips are separated by a void, wherein said void is complimentary in dimension to said lip of said first flange.

2. The spinal fusion implant of claim 1, wherein each of said first and second flanges extend generally angularly from said body at an angle between 15 and 75 degrees, inclusive, relative to the planes of said first and second contact surfaces.

3. The spinal fusion implant of claim 1, wherein said first and second contact surfaces are dimensioned to contact an endplate of at least one of said first and second vertebral bodies.

4. The spinal fusion implant of claim 1, wherein at least one of said first and second contact surfaces and said first and second lateral sides includes at least one aperture extending therethrough.

5. The spinal fusion implant of claim 4, wherein said at least one aperture has a shape comprising at least one of rectangular, oblong, triangular, circular, polygonal and any combination of rectangular, oblong, triangular, circular, polygonal.

6. The spinal fusion implant of claim 1, wherein said lip of said first flange includes at least one aperture configured to receive a bone anchor element.

7. The spinal fusion implant of claim 6, wherein said bone anchor element includes at least one of a bone screw, nail, pin and hook.

8. The spinal fusion implant of claim 1, wherein each lip of said pair of lips comprising said second flange include at least one aperture configured to receive a bone anchor element.

9. The spinal fusion implant of claim 8, wherein said bone anchor element includes at least one of a bone screw, nail, pin and hook.

10. The spinal fusion implant of claim 1, wherein said lip of said first flange is configured to engage a cortical bone portion of said first vertebral body.

11. The spinal fusion implant of claim 10, wherein said cortical bone portion is located along an anterior aspect of said first vertebral body.

12. The spinal fusion implant of claim 1, wherein said pair of lips of said second flange are configured to engage a cortical bone portion of said second vertebral body.

13. The spinal fusion implant of claim 12, wherein said cortical bone portion is located along an anterior aspect of said second vertebral body.

14. The system of claim 1, wherein said cortical bone portion is located along an anterior aspect of said second vertebral body.

15. The spinal fusion implant of claim 1, wherein the trailing end includes at least one fusion aperture extending therethrough.

16. A system for effectuating fusion between a first vertebral body and a second vertebral body, comprising:
an implant including a body portion having first and second contact surfaces, first and second lateral sides, a leading end and a trailing end, a first flange comprising a lip extending away from said body portion at an interface between said first contact surface and said trailing end, said lip being generally centered between said first and second lateral sides and extending laterally to points short of said first and second sides, a second flange comprising a pair of lips extending away from said body portion at an interface between said second contact surface and said trailing end, said first lip extending laterally from said first lateral surface to a point short of the center of said trailing end and said second lip extending generally laterally from said second lateral side to a point short of the center of said trailing end such that said first and second lips are separated by a void, wherein said void is complimentary in dimension to said lip of said first flange; and
a plurality of bone anchor elements.

17. The spinal fusion implant of claim 16, wherein each of said first and second flanges extend generally angularly from said body at an angle between 15 and 75 degrees, inclusive, relative to the planes of said first and second contact surfaces.

18. The system of claim 16, wherein said first and second contact surfaces are dimensioned to contact an endplate of at least one of said first and second vertebral bodies.

19. The system of claim 16, wherein at least one of said first and second contact surfaces and said first and second lateral sides includes at least one aperture extending therethrough.

20. The system of claim 16, wherein each of said lip of said first flange and said pair of lips of said second flange include at least one aperture configured to receive said bone anchor element.

21. The system of claim 16, wherein said bone anchor element includes at least one of a bone screw, nail, pin and hook.

22. The system of claim 16, wherein said lip of said first flange is configured to engage a cortical bone portion of said first vertebral body.

23. The system of claim 22, wherein said cortical bone portion is located along an anterior aspect of said first vertebral body.

24. The system of claim 16, wherein said pair of lips of said second flange are configured to engage a cortical bone portion of said second vertebral body.

25. The system of claim 16 wherein the trailing end includes at least one fusion aperture extending therethrough.

* * * * *